US006979535B2

(12) United States Patent
Alizon et al.

(10) Patent No.: US 6,979,535 B2
(45) Date of Patent: Dec. 27, 2005

(54) HUMAN IMMUNODEFICIENCY VIRUS TYPE 2 (HIV-2) ENV POLYPEPTIDE AND DIAGNOSTIC ASSAYS

(75) Inventors: Marc Alizon, Paris (FR); Luc Montagnier, Le Plessy Robinson (FR); Denise Guetard, Paris (FR); Francois Clavel, Rockville, MD (US); Pierre Sonigo, Gutenberg (FR); Mireille Guyader, Laugier (FR)

(73) Assignee: Institut Pasteur (FR)

( * ) Notice: Subject to any disclaimer, the term of this patent is extended or adjusted under 35 U.S.C. 154(b) by 447 days.

(21) Appl. No.: 10/133,357

(22) Filed: Apr. 29, 2002

(65) Prior Publication Data

US 2003/0082523 A1 May 1, 2003

Related U.S. Application Data

(60) Division of application No. 09/191,384, filed on Nov. 13, 1998, now Pat. No. 6,514,691, which is a continuation of application No. 08/468,093, filed on Jun. 6, 1995, now Pat. No. 5,866,319, which is a continuation of application No. 07/754,903, filed on Sep. 4, 1991, now Pat. No. 5,578,715, which is a division of application No. 07/003,764, filed on Jan. 16, 1987, now Pat. No. 5,051,496, which is a continuation-in-part of application No. 06/933,184, filed on Nov. 21, 1986, now abandoned, which is a continuation-in-part of application No. 06/916,080, filed on Oct. 6, 1986, now abandoned, which is a continuation-in-part of application No. 06/835,228, filed on Mar. 3, 1986, now Pat. No. 4,839,288.

(30) Foreign Application Priority Data

| Jan. 22, 1986 | (FR) | 86 00911 |
| Jan. 22, 1986 | (FR) | 86 00910 |
| Feb. 3, 1986 | (FR) | 86 01985 |
| Feb. 6, 1986 | (FR) | 86 01635 |

(51) Int. Cl.$^7$ .................... C12Q 1/70; A61K 39/21
(52) U.S. Cl. .............. 435/5; 424/188.1; 424/208.1; 530/530; 530/325
(58) Field of Search ................ 424/188.1, 208.1

(56) References Cited

U.S. PATENT DOCUMENTS

| 4,520,113 A | 5/1985 | Gallo et al. ............. 436/504 |
| 4,588,681 A | 5/1986 | Sawada et al. ............ 435/5 |
| 4,629,783 A | 12/1986 | Cosand ................. 530/324 |
| 4,647,773 A | 3/1987 | Gallo et al. ............. 435/239 |
| 4,652,599 A | 3/1987 | Gallo et al. ............. 435/239 |
| 4,708,818 A | 11/1987 | Montagnier et al. ......... 435/5 |
| 4,839,288 A | 6/1989 | Montagnier et al. ...... 435/235 |
| 5,051,496 A * | 9/1991 | Alizon et al. ............ 530/324 |
| 5,055,391 A | 10/1991 | Montagnier et al. ......... 435/5 |
| 5,079,342 A | 1/1992 | Alizon et al. ............ 530/324 |
| 5,223,423 A | 6/1993 | Franchini et al. ......... 435/236 |
| 5,306,614 A | 4/1994 | Alizon et al. ............. 435/5 |
| 5,310,651 A | 5/1994 | Alizon et al. ............. 435/6 |
| 5,374,518 A | 12/1994 | Hunt et al. ............... 435/5 |
| 5,480,966 A | 1/1996 | Somme et al. ........... 530/324 |
| 5,670,309 A | 9/1997 | Norrby et al. ............. 435/5 |
| 5,702,918 A | 12/1997 | Bannwarth et al. ....... 435/69.3 |

FOREIGN PATENT DOCUMENTS

| EP | 0 316 695 B1 | 3/1993 |
| EP | 0 185 444 B1 | 12/1993 |
| EP | 0 187 041 B1 | 5/1996 |
| WO | WO 84/04327 | 11/1984 |
| WO | WO 85/04897 | 11/1985 |
| WO | WO 86/01834 | 3/1986 |
| WO | WO 86/02383 | 4/1986 |
| WO | WO 86/02930 | 5/1986 |
| WO | WO 86/04423 | 7/1986 |
| WO | WO 87/02892 | 5/1987 |

OTHER PUBLICATIONS

Barin et al., Serological evidence for virus related to simian T–lymphotropic retrovirus III in residents of West Africa, The Lancet 2:1397–1389 (1985).
Barre–Sinoussi et al., Isolation of a T–lymphotropic retrovirus from a Patient at risk for Acquired Immune Deficiency Syndrome (AIDS), Science 2200:868–871 (1983).
Chakrabarti et al., Sequence of simian immunodeficiency virus from macaque and its relationship to other human and simian retroviruses, Nature 328:543–547 (1987).
Clavel et al., Isolation of a new human retrovirus from West African pateients with AIDS, Science 233:343–346 (1986).
Clavel et al., LAV Type II: a second retroviruses associated with AIDS in West Africa, C.R. Acad. Sc. Paris, t. 302, Série III, 13:485–488 (1986).
Clavel et al., Molecular cloning and polymorphism of the human immune deficiency virus type 2, Nature 324:691–694 (1986).
Coffin et al., Human immunodefiency viruses, Science 232:697 (1986).
Daniel et al., Isolation of T–cell tropic HTLV–III–like retrovirus from macaques, Science 228:1201–1204 (1985).
Essex et al., Nature 331:621–622 (1988).
Fultz et al., Isolation of a T–lymphotropic retrovirus from naturally infected sooty mangabey monkeys (*Cercocebus atys*), Proc. Nat'l. Acad. Sci. USA, 83:5286–5290 (1986).
Gallo et al., The AIDS virus, Scientific American, pp. 47–56 (1987).
Guyader et al., Genome organization and transactivation of the human immunodeficiency virus type 2, Nature 326:662–669 (1987).

(Continued)

*Primary Examiner*—Jeffrey S. Parkin
(74) *Attorney, Agent, or Firm*—Finnegan, Henderson, Farabow, Garrett & Dunner, L.L.P.

(57) ABSTRACT

A method for diagnosing an HIV-2 (LAV-II) infection and a kit containing reagents for the same is disclosed. These reagents include cDNA probes which are capable of hybridizing to at least a portion of the genome of HIV-2. In one embodiment, the DNA probes are capable of hybridizing to the entire genome of HIV-2. These reagents also include polypeptides encoded by some of these DNA sequences.

9 Claims, 5 Drawing Sheets

OTHER PUBLICATIONS

Kanki et al., Isolation of T–lymphotropic retrovirus related to HTLV–III/LAV from wild–caught African green monkeys, Science 230:951–954 (1985).

Kanki et al., New human T–lymphotropic retrovirus related to simian T–lymphotropic virus type III (STLV–III$_{AGM}$), Science 232:238–243 (1986).

Kanki et al., Serologic identification and characterization of a macaque t–lymphotropic retrovirus closely related to HTLV–III, Science 228:1199–1201 (1985).

Kestler et al., Comparison of simian immunodeficiency virus isolates, Nature 331:619–621 (1988).

Klatzmann et al., T–lymphocyte T4 molecule behaves as the receptor for human retrovirus LAV, Nature 312:767–768 (1984).

Probing the AIDS Virus and its relatives, Science 236:1523–1524 (1987).

Mitsuya et al., Protection of T cells against infectivity and cytopathic effect of HTLV–III In Vitro, Retroviruses in human lymphoma/leukemia, M. Miwa et al. (eds.) pp. 277–288 Japan Sci. Soc. Press, Tokyo/VNU Science Press, Utrecht (1985).

Mulder et al., A case of mistaken non–identity, Nature 331:562–563 (1998).

Sandstrom et al., Antiviral therapy in AIDS, clinical pharmacological properties and therapeutic experience to date, Drugs 34:372–390 (1987).

Stryer, Biochemistry (W.H. Freeman and Company, San Francisco), pp. 761–763 (1975).

Wang et al., Detection of antibodies to human T–lymphotropic virus type III by using a synthetic peptide of 21 amino acid residues corresponding to a highly antigenic segment of gp31 envelope protein, Proc. Nat'l Acad. Sci., USA, 83:6159–6163 (1986).

* cited by examiner

FIG. 2A
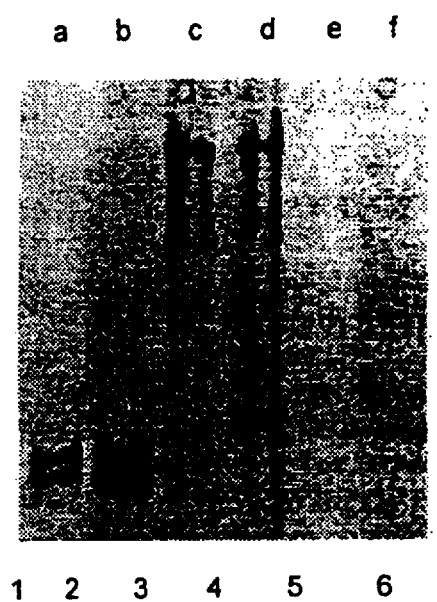
FIG. 2B
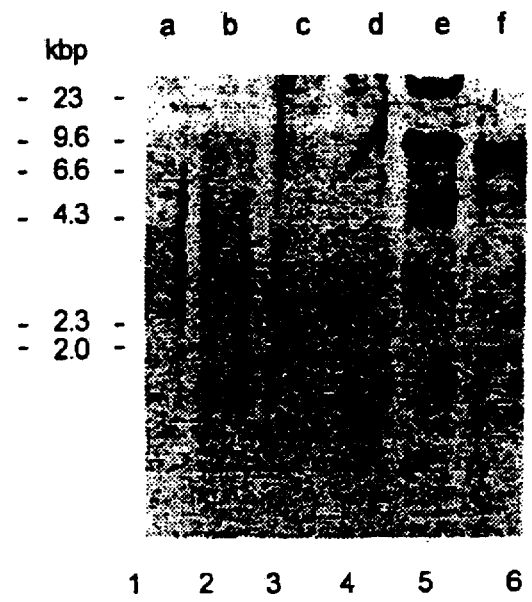
FIG. 2C
FIG. 2D

HUMAN IMMUNODEFICIENCY VIRUS TYPE 2 (HIV-2) ENV POLYPEPTIDE AND DIAGNOSTIC ASSAYS

This is a division of application Ser. No. 09/191,384, filed Nov. 13, 1998 now U.S. Pat. No. 6,514,691; Cont. of 08/468,093 (Jun. 6, 1995), now U.S. Pat. No. 5,866,319; Cont. of 07/754,903 (Sep. 4, 1991), now U.S. Pat. No. 5,578,715; Div. of 07/003,764 (Jan. 16, 1987), now U.S. Pat. No. 5,051,496; CIP of 06/933,184 (Nov. 21, 1986), now abandoned CIP of 06/916,080 (Oct. 6, 1986), now abandoned; CIP of 06/835,228 (Mar. 3, 1986), now U.S. Pat. 4,839,288 all of which are incorporated herein by reference.

BACKGROUND OF THE INVENTION

The invention relates to cloned DNA sequences analogous to the genomic RNA of a virus known as Lymphadenopathy-Associated Virus II ("LAV-II"), a process for the preparation of these cloned DNA sequences, and their use as probes in diagnostic kits. In one embodiment, the invention relates to a cloned DNA sequence analogous to the entire genomic RNA of HIV-2 and its use as a probe. The invention also relates to polypeptides with amino acid sequences encoded by these cloned DNA sequences and the use of these polypeptides in diagnostic kits.

According to recently adopted nomenclature, as reported in Nature, May 1986, a substantially-identical group of retroviruses which has been identified as one causative agent of AIDS are now referred to as Human Immunodeficiency Viruses I (HIV-1). This previously-described group of retroviruses includes Lymphadenopathy-Associated Virus I (LAV-I), Human T-cell Lymphotropic Virus-III (HTLV-III), and AIDS-Related Virus (ARV).

Lymphadenopathy-Associated Virus II has been described in U.S. application Ser. No. 835,228, which was filed Mar. 3, 1986, and is specifically incorporated herein by reference. Because LAV-II is a second, distinct causative agent of AIDS, LAV-II properly is classifiable as a Human Immunodeficiency Virus II (HIV-2). Therefore, "LAV-II" as used hereinafter describes a particular genus of HIV-2 isolates.

While HIV-2 is related to HIV-1 by its morphology, its tropism and its in vitro cytopathic effect on CD4 (T4) positive cell lines and lymphocytes, HIV-2 differs from previously described human retroviruses known to be responsible for AIDS. Moreover, the proteins of HIV-1 and 2 have different sizes and their serological cross-reactivity is restricted mostly to the major core protein, as the envelope glycoproteins of HIV-2 are not immune precipitated by HIV-1-positive sera except in some cases where very faint cross-reactivity can be detected. Since a significant proportion of the HIV infected patients lack antibodies to the major core protein of their infecting virus, it is important to include antigens to both HIV-1 and HIV-2 in an effective serum test for the diagnosis of the infection by these viruses.

HIV-2 was first discovered in the course of serological research on patients native to Guinea-Bissau who exhibited clinical and immunological symptoms of AIDS and from whom sero-negative or weakly sero-positive reactions to tests using an HIV-1 lysate were obtained. Further clinical studies on these patients isolated viruses which were subsequently named "LAV-II."

One LAV-II isolate, subsequently referred to as LAV-II MIR, was deposited at the Collection Nationale des Cultures de Micro-Organismes (CNCM) at the Institut Pasteur in Paris, France on Dec. 19, 1985 under Accession No. I-502 and has also been deposited at the British ECA CC under No. 87.001.001 on Jan. 9, 1987. A second LAV-II isolate was deposited at CNCM on Feb. 21, 1986 under Accession No. I-532 and has also been deposited at the British ECA CC under No. 87.001.002 on Jan. 9, 1987. This second isolate has been subsequently referred to as LAV-II ROD. Other isolates deposited at the CNCM on Dec. 19, 1986 are HIV-2 IRMO (No. I-642) and HIV-2 EHO (No. I-643). Several additional isolates have been obtained from West African patients, some of whom have AIDS, others with AIDS-related conditions and others with no AIDS symptoms. All of these viruses have been isolated on normal human lymphocyte cultures and some of them were thereafter propagated on lymphoid tumor cell lines such as CEM and MOLT.

Due to the sero-negative or weak sero-positive results obtained when using kits designed to identify HIV-1 infections in the diagnosis of these new patients with HIV-2 disease, it has been necessary to devise a new diagnostic kit capable of detecting HIV-2 infection, either by itself or in combination with an HIV-1 infection. The present inventors have, through the development of cloned DNA sequences analogous to at least a portion of the genomic RNA of LAV-II ROD viruses, created the materials necessary for the development of such kits.

SUMMARY OF THE INVENTION

As noted previously, the present invention relates to the cloned nucleotide sequences homologous or identical to at least a portion of the genomic RNA of HIV-2 viruses and to polypeptides encoded by the same. The present invention also relates to kits capable of diagnosing an HIV-2 infection.

Thus, a main object of the present invention is to provide a kit capable of diagnosing an infection caused by the HIV-2 virus. This kit may operate by detecting at least a portion of the RNA genome of the HIV-2 virus or the provirus present in the infected cells through hybridization with a DNA probe or it may operate through the immunodiagnostic detection of polypeptides unique to the HIV-2 virus.

Additional objects and advantages of the present invention will be set forth in part in the description which follows, or may be learned from practice of the invention. The objects and dvantages may be realized and attained by means of the instrumentalities and combinations particularly pointed out in the appended claims.

To achieve these objects and in accordance with the purposes of the present invention, cloned DNA sequences related to the entire genomic RNA of the LAV-II virus are set forth. These sequences are analogous specifically to the entire genome of the LAV-II ROD strain.

To further achieve the objects and in accordance with the purposes of the present invention, a kit capable of diagnosing an HIV-2 infection is described. This kit, in one embodiment, contains the cloned DNA sequences of this invention which are capable of hybridizing to viral RNA or analogous DNA sequences to indicate the presence of an HIV-2 infection. Different diagnostic techniques can be used which include, but are not limited to: (1) Southern blot procedures to identify cellular DNA which may or may not be digested with restriction enzymes; (2) Northern blot techniques to identify RNA extracted from cells; and (3) dot blot techniques, i.e., direct filtration of the sample through an ad hoc membrane such as nitrocellulose or nylon without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by centrifugation as accomplished in the "CYTODOT" procedure as described in a booklet published by Schleicher and Schull.

In an alternate embodiment, the kit contains the polypeptides created using these cloned DNA sequences. These polypeptides are capable of reacting with antibodies to the HIV-2 virus present in sera of infected individuals, thus yielding an immunodiagnostic complex.

It is understood that both the foregoing general description and the following detailed description are exemplary and explanatory only and are not restrictive of the invention as claimed. The accompanying drawings, which are incorporated in and constitute a part of the specification, illustrate one embodiment of the invention and, together with the description, serve to explain the principles of the invention.

BRIEF DESCRIPTION OF THE DRAWINGS

FIG. 1 generally depicts the nucleotide sequence of a cloned complementary DNA (cDNA) to the genomic RNA of HIV-2.

In FIG. 1B, the symbols B, H, Ps and Pv refer to the restriction sites BamHI, HindIII, PstI and PvuII, respectively.

FIG. 2 generally depicts the HIV-2 specificity of the E2 clone. FIGS. 2A and B specifically depict a Southern blot of DNA extracted from CEM cells infected with the following isolates: HIV-2$_{ROD}$ (a,c) HIV-2$_{DUL}$ (b,d) and HIV-1$_{BRU}$ (e,f). Blots a,b,f are PstI digested. Blots c,d,e are undigested. FIGS. 2C and D specifically depict dot blot hybridization of pelleted virions from CEM cells infected by the HIV-1$_{BRU}$ (1), Simian Immunodeficiency Virus (SIV) isolate Mm 142-83 (3), HIV-2$_{DUL}$ (4), HIV-2$_{ROD}$ (5), and HIV-1$_{ELI}$ (6). Dot 2 is a pellet from an equivalent volume of supernatant from uninfected CEM. Thus, FIGS. 2A and C depicts hybridization with the HIV-2 cDNA (E2) and FIGS. 2B and D depicts hybridization to an HIV-1 probe consisting of a 9.2 Kb SacI insert from HIV-1$_{BRU}$.

FIG. 3 generally depicts a restriction map of the HIV-2 ROD genome and its homology to HIV-1. In FIG. 3A, the open boxes represent viral sequences, the LTR are filled, and the dotted boxes represent cellular flanking sequences (not mapped). Only some characteristic restriction enzyme sites are indicated. λROD 27 and λ35 are derived from integrated proviruses while λROD 4 is derived from a circular viral DNA. The portion of the lambda clones that hybridzes to the cDNA E2 is indicated below the maps. A restriction map of the λROD isolate was reconstructed from these three lambda clones. In this map, the restriction sites are identified as follows: B: BamHI; E: EcoRI; H: HindIII; K: KpnI; Ps: PstI; Pv: PvuII; S: SacI; X: XbaI. R and L are the right and left BamHI arms of the lambda L47.1 vector.

FIG. 4 generally depicts the restriction map polymorphism in different HIV-2 isolates and shows comparison of HIV-2 to SIV.

DETAILED DESCRIPTION OF THE PREFERRED EMBODIMENTS

Reference will now be made in detail to the presently preferred embodiments of the invention, which, together with the following examples, serve to explain the principles of the invention.

Figures 1A, 1B:
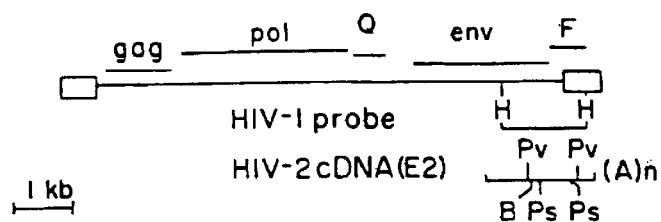
FIG. 1A depicts the genetic organization of HIV-1, position of the HIV-1 HindIII fragment used as a probe to screen the cDNA library, and restriction map of the HIV-2 cDNA clone, E2.
FIG. 1B depicts the nucleotide sequence of the 3' end of the 3' LTR of HIV-2. The corresponding region of the HIV-1 LTR was aligned using the Wilbur and Lipman algorithm (window: 10; K-tuple: 7; gap penalty: 3) as described by Wilbur and Lipman in Proc. Natl. Acad. Sci. USA 80: 726–730 (1983), specifically incorporated herein by reference. The U3-R junction in HIV-1 is indicated and the poly A addition signal and potential TATA promoter regions are boxed.

The genetic structure of the HIV-2 virus has been analyzed by molecular cloning according to the method set forth herein and in the Examples. A restriction map of the genome of this virus is included in FIG. 4. In addition, the partial sequence of a cDNA complementary to the genomic RNA of the virus has been determined. This cDNA sequence information is included in FIG. 1.

Also contained herein is data describing the molecular cloning of the complete 9.5 kb genome of HIV-2, data describing the observation of restriction map polymorphism between different isolates, and an analysis of the relationship between HIV-2 and other human and simian retroviruses. From the totality of these data, diagnostic probes can be discerned and prepared.

Generally, to practice one embodiment of the present invention, a series of filter hybridizations of the HIV-2 RNA genome with probes derived from the complete cloned HIV-1 genome and from the gag and pol genes were conducted. These hybridizations yielded only extremely weak signals even in conditions of very low stringency of hybridization and washing. Thus, it was found to be difficult to assess the amount of HIV-2 viral and proviral DNA in infected cells by Southern blot techniques.

Therefore, a complementary DNA (cDNA) to the HIV-2 genomic RNA initially was cloned in order to provide a specific hybridization probe. To construct this cDNA, an oligo (dT) primed cDNA first-strand was made in a detergent-activated endogenous reaction using HIV-2 reverse transcriptase with virions purified from supernatants of infected CEM cells. The CEM cell line is a lymphoblastoid CD4+ cell line described by G. E. Foley et al. in Cancer 18: 522–529 (1965), specifically incorporated herein by reference. The CEM cells used were infected with the isolate ROD and were continuously producing high amounts of HIV-2.

After second-strand synthesis, the cDNAs were inserted into the TG130 m13 bacteria phage vector. A collection of $10^4$ M13 recombinant phages was obtained and screened in situ with an HIV-1 probe spanning 1.5 kb. of the 3' end of the $LAV_{BRU}$ isolate (depicted in FIG. 1A). Some 50 positive plaques were detected, purified, and characterized by end sequencing and cross-hybridizing the inserts. This procedure is described in more detail in Example 1 and in FIG. 1.

The different clones were found to be complementary to the 3' end of a polyadenylated RNA having the AATAAA signal about 20 nucleotides upstream of the poly A tail, as found in the long terminal repeat (LTR) of HIV-1. The LTR region of HIV-1 has been described by S. Wain Hobson et al. in Cell 40: 9–17 (1985), specifically incorporated herein by reference. The portion of the HIV-2 LTR that was sequenced was related only distantly to the homologous domain in HIV-1 as demonstrated in FIG. 1 B. Indeed, only about 50% of the nucleotides could be aligned and about a hundred insertions/deletions need to be introduced. In comparison, the homology of the corresponding domains in HIV-1 isolates from USA and Africa is greater than 95% and no insertions or deletions are seen.

The largest insert of this group of M13 clones was a 2 kb. clone designated E2. Clone E2 was used as a probe to demonstrate its HIV-2 specificity in a series of filter hybridization experiments. Firstly, this probe could detect the genomic RNA of HIV-2 but not HIV-1 in stringent conditions as shown in FIG. 2, C and D. Secondly, positive signals were detected in Southern blots of DNA from cells infected with the ROD isolate as well as other isolates of HIV-2 as shown in FIG. 2, A and FIG. 4, A. No signal was detected with DNA from uninfected cells or HIV-1 infected cells, confirming the exogenous nature of HIV-2. In undigested DNA from HIV-2 infected cells, an approximately 10 kb. species, probably corresponding to linear unintegrated viral DNA, was principally detected along with a species with an apparent size of 6 kb., likely to be the circular form of the viral DNA. Conversely, rehybridization of the same filter with an HIV-1 probe under stringent conditions showed hybridization to HIV-1 infected cells only as depicted in FIG. 2, B.

To isolate the remainder of the genome of HIV-2, a genomic library in lambda phage L47.1 was constructed. Lambda phage L47.1 has been described by W. A. M. Loenen et al. in Gene 10: 249–259 (1980), specifically incorporated herein by reference. The genomic library was constructed with a partial Sau3AI restriction digest of the DNA from the CEM cell line infected with $HIV-2_{ROD}$.

About $2 \times 10^6$ recombinant plaques were screened in situ with labelled insert from the E2 cDNA clone. Ten recombinant phages were detected and plaque purified. Of these phages, three were characterized by restriction mapping and Southern blot hybridization with the E2 insert and probes from its 3' end (LTR) or 5' end (envelope), as well as with HIV-1 subgenomic probes. In this instance, HIV-1 probes were used under non-stringent conditions.

Figure 3A:
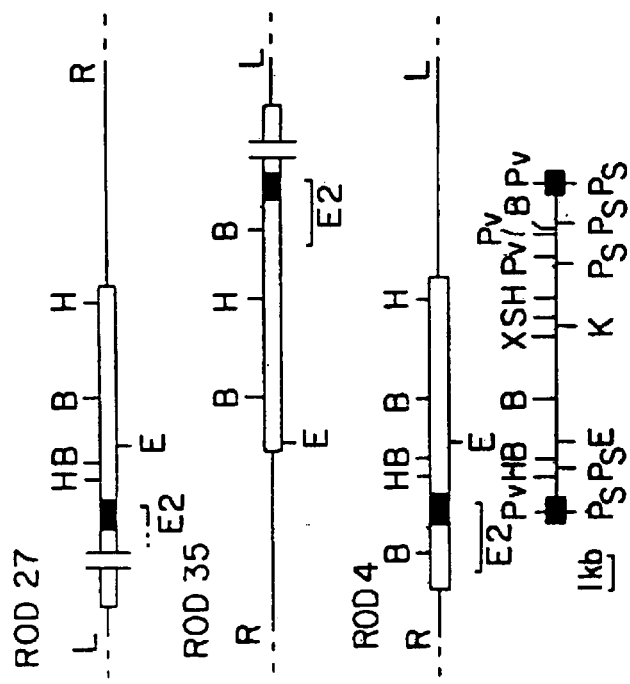
FIG. 3A specifically depicts the organization of three recombinant phage lambda clones, ROD 4, ROD 27, and ROD 35.
Figure 3B:
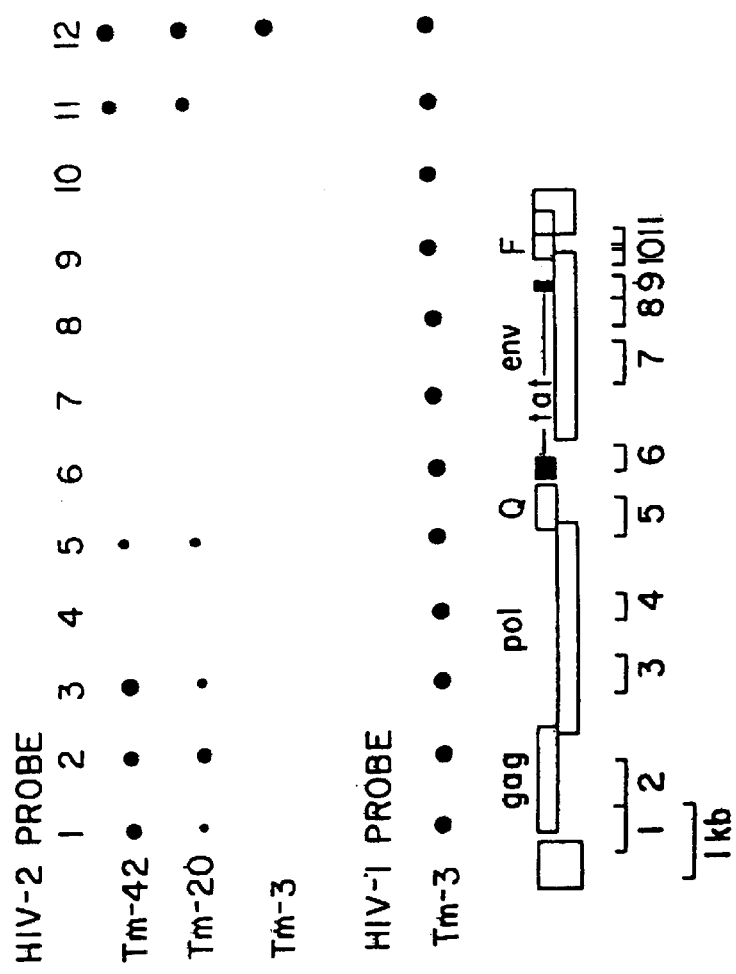
FIG. 3B specifically depicts dots 1–11 which correspond to the single-stranded DNA form of M13 subclones from the HIV-1$_{BRU}$ cloned genome. Their size and position on the HIV-1 genome, determined by sequencing is shown below the figure. Dot 12 is a control containing lambda phage DNA. The dot-blot was hybridized in low stringency conditions as described in Example 1 with the complete lambda λROD 4 clone as a probe, and successively washed in 2×SSC, 0.1% SDS at 25° C. (Tm −42° C.), 1×SSC, 0.1% SDS at 60° C. (Tm −20° C.), and 0.1×SSC, 0.1% SDS at 60° C. (Tm −30° C.) and exposed overnight. A duplicate dot blot was hybridized and washed in stringent conditions (as described in Example 2) with the labelled lambda J19 clone carrying the complete HIV-1$_{BRU}$ genome. HIV-1 and HIV-2 probes were labelled the same specific activity ($10^8$ cpm/g.).

A clone carrying a 9.5 kb. insert and derived from a circular viral DNA was identified as containing the complete genome and designated λROD 4. Two other clones, λROD 27 and λROD 35 were derived from integrated proviruses and found to carry an LTR and cellular flanking sequences and a portion of the viral coding sequences as shown in FIG. 3, A.

Fragments of the lambda clones were subcloned into a plasmid vector p UC 18.

Plasmid pROD 27-5' is derived from λROD 27 and contains the 5' 2 Kb of the HIV-2 genome and cellular flanking sequences (5' LTR and 5' viral coding sequences to the EcoRI site)

Plasmid pROD 4.8 is dervied from λROD 4 and contains the about 5 kb HindIII fragments that is the central part of the HIV-2 genome.

Plasmid pROD 27-5' and p ROD 4.8 inserts overlap.

Plasmid pROD 4.7 contains a HindIII 1.8 Kb fragment from λROD 4. This fragment is located 3' to the fragment subcloned into pROD 4.8 and contains about 0.8 Kb of viral coding sequences and the part of the lambda phage (λL47.1) left arm located between the BamHI and HindIII cloning sites.

Plasmid pROD 35 contains all the HIV-2 coding sequences 3' to the EcoRI site, the 3' LTR and about 4 Kb of cellular flanking sequences.

Figure 5:
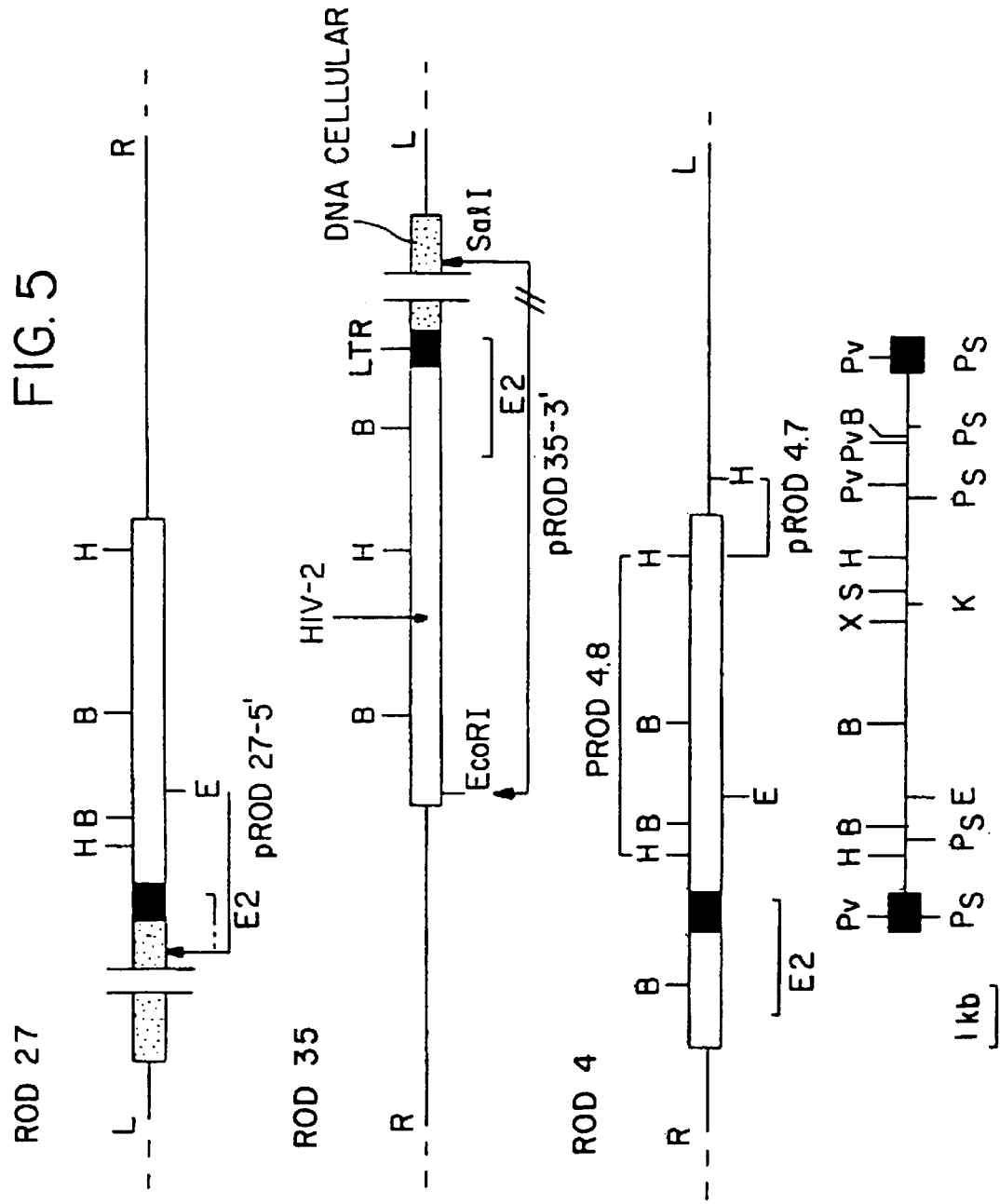
FIG. 5 depicts plasmids λROD 27, λROD 35 and λROD 4.

Plasmid pROD 27-5' and pROD 35 in E. coli strain HB 101 are deposited respectively under No. 1-626 and 1-633 at the CNCM, and have also been deposited at the NCIB (British Collection). These plasmids are depicted in FIG. 5. Plasmid pROD 4.7 and PROD 4.8 in E. coli strain TG1 are deposited respectively under No. 1-627 and 1-628 at the CNCM.

To reconstitute the complete HIV-2 ROD genome, pROD 35 is linearized with EcoRI and the EcoRI insert of pROD 27-5' is ligated in the correct orientation into this site.

The relationship of HIV-2 to other human and simian retroviruses was surmised from hybridization experiments. The relative homology of the different regions of the HIV-1 and 2 genomes was determined by hybridization of fragments of the cloned HIV-1 genome with the labelled λROD 4 expected to contain the complete HIV-2 genome (FIG. 3, B). Even in very low stringency conditions (Tm–42° C.), the hybridization of HIV-1 and 2 was restricted to a fraction of their genomes, principally the gag gene (dots 1 and 2), the reverse transcriptase domain in pol (dot 3), the end of pol and the Q (or sor) genes (dot 5) and the F gene (or 3' orf) and 3' LTR (dot 11). The HIV-1 fragment used to detect the HIV-2 cDNA clones contained the dot 11 subclone, which hybridized well to HIV-2 under non-stringent conditions. Only the signal from dot 5 persisted after stringent washing. The envelope gene, the region of the tat gene and a part of pol thus seemed very divergent. These data, along with the LTR sequence obtained (FIG. 1, B), indicated that HIV-2 is not an envelope variant of HIV-1 as described by Alizon et al., Cell 40:63–74 (1986).

It was observed that HIV-2 is related more closely to the Simian Immunodeficiency Virus (SIV) than it is to HIV-1. This correlation has been described by F. Clavel et al. in C.R. Acad. Sci. (Paris) 302: 485–488 (1986) and F. Clavel et al. in Science 233: 343–346 (1986), both of which are specifically incorporated herein by reference. Simian Immunodeficiency Virus (also designated Simian T-cell Lymphotropic Virus Type 3, STLV-3) is a retrovirus first isolated from captive macaques with an AIDS-like disease in the USA. This simian virus has been described by M. D. Daniel et al. in Science 228: 1201–1204 (1985), specifically incorporated herein by reference.

All the SIV proteins, including the envelope, are immune precipitated by sera from HIV-2 infected patients, whereas the serological cross-reactivity of HIV-1 to 2 is restricted to the core proteins. However SIV and HIV-2 can be distinguished by slight differences in the apparent molecular weight of their proteins.

In terms of nucleotide sequence, it also appears that HIV-2 is closely related to SIV. The genomic RNA of SIV can be detected in stringent conditions as shown in FIG. 2, C by HIV-2 probes corresponding to the LTR and 3' end of the genome (E2) or to the gag or pol genes. Under the same conditions, HIV-1 derived probes do not detect the SIV genome as shown in FIG. 2, D.

In Southern blots of DNA from SIV-infected cells, a restriction pattern clearly different from HIV-2$_{ROD}$ and other isolates is seen. All the bands persist after a stringent washing, even though the signal is considerably weakened, indicating a sequence homology throughout the genomes of HIV-2 and SIV. It has recently been shown that baboons and macaques could be infected experimentally by HIV-2, thereby providing an interesting animal model for the study of the HIV infection and its preventive therapy. Indeed, attempts to infect non-human primates with HIV-1 have been successful only in chimpanzees, which are not a convenient model.

Figure 4A:
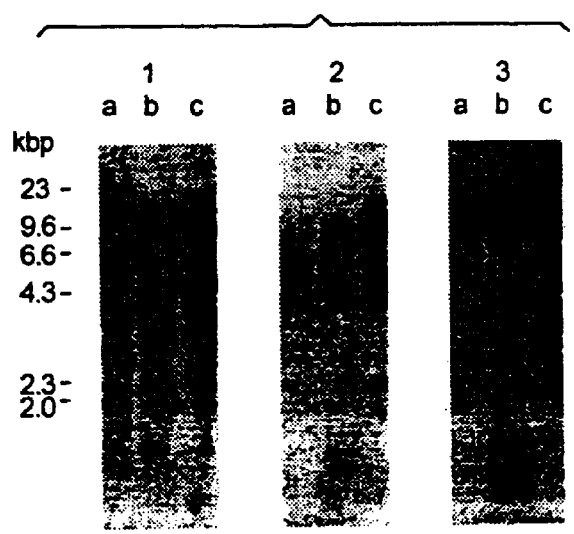
FIG. 4A specifically depicts DNA (20 ug. per lane) from CEM cells infected by the isolate HIV-2$_{DUL}$ (panel 1) or peripheral blood lymphocytes (PBL) infected by the isolates HIV-2$_{GOM}$ (panel 2) and HIV-2$_{MIR}$ (panel 3) digested with: EcORI (a), PstI (b), and HindIII (c). Much less viral DNA was obtained with HIV-2 isolates propagated on PBL. Hybridization and washing were in stringent conditions, as described in Example 2, with $10^6$ cpm/ml. of each of the E2 insert (cDNA) and the 5 kb. HindIII fragment of λROD 4, labelled to $10^9$ cpm/ug.
Figure 4B:
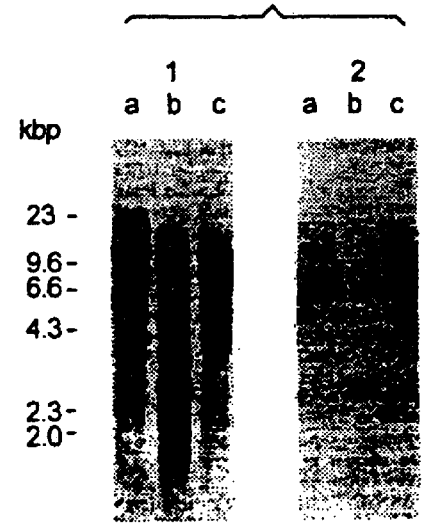
FIG. 4B specifically depicts DNA from HUT 78 (a human T lymphoid cell line) cells infected with SIV Mm 142-83. The same amounts of DNA and enzymes were used as indicated in panel A. Hybridization was performed with the same probe as in A, but in non-stringent conditions. As described in Example 1 washing was for one hour in 2×SSC, 0.1% SDS at 40° C. (panel 1) and after exposure, the same filter was re-washed in 0.1×SSC, 0.1% SDS at 60° C. (panel 2). The autoradiographs were obtained after overnight exposition with intensifying screens.

From an initial survey of the restriction maps for certain of the HIV-2 isolates obtained according to the methods described herein, it is already apparent that HIV-2, like HIV-1, undergoes restriction site polymorphism. FIG. 4 A depicts examples of such differences for three isolates, all different one from another and from the cloned HIV-2$_{ROD}$. It is very likely that these differences at the nucleotide level are accompanied by variations in the amino-acid sequence of the viral proteins, as evidenced in the case of HIV-1 and described by M. Alizon et al. in Cell 46: 63–74 (1986), specifically incorporated herein by reference. It is also to be expected that the various isolates of HIV-2 will exhibit other minor amino acid heterogeneities. See, for example, Clavel et al., Nature 324 (18):691–695 (1986), specifically incorporated herein by reference.

Further, the chacterization of HIV-2 will also delineate the domain of the envelope glycoprotein that is responsible for the binding of the surface of the target cells and the subsequent internalization of the virus. This interaction was shown to be mediated by the CD4 molecule itself in the case of HIV-1 and similar studies tend to indicate that HIV-2 uses the same receptor. Thus, although there is wide divergence between the env genes of HIV-1 and 2, small homologous domains of the envelopes of the two HIV could represent a candidate receptor binding site. This site could constitute a target for use to raise a protective immune response against this group of retroviruses.

From the data discussed herein, certain nucleotide sequences have been identified which are capable of being used as probes in diagnostic methods to obtain the immunological reagents necessary to diagnose an HIV-2 infection. In particular, these sequences may be used as probes in hybridization reactions with the genetic material of infected patients to indicate whether the RNA of the HIV-2 virus is present in these patient's lymphocytes or whether an analogous DNA is present. In this embodiment, the test methods which may be utilized include Northern blots, Southern blots and dot blots. One particular nucleotide sequence which may be useful as a probe is the combination of the 5 kb. HindIII fragment of ROD 4 and the E2 cDNA used in FIG. 4.

In addition, the genetic sequences of the HIV-2 virus may be used to create the polypeptides encoded by these sequences. Specifically, these polypeptides may be created by expression of the cDNA obtained according to the teachings herein in hosts such as bacteria, yeast or animal cells. These polypeptides may be used in diagnostic tests such as immunofluorescence assays (IFA), radioimmunoassays (RIA) and Western Blot tests.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

In addition, monoclonal antibodies to these polypeptides or fragments thereof may be created. The monoclonal antibodies may be used in immunodiagnostic tests in an analogous manner as the polypeptides described above.

The polypeptides of the present invention may also be used as immunogenic reagents to induce protection against infection by HIV-2 viruses. In this embodiment, the polypeptides produced by recombinant-DNA techniques would function as vaccine agents.

Also, the polypeptides of this invention may be used in competitive assays to test the ability of various antiviral agents to determine their ability to prevent the virus from fixing on its target.

Thus, it is to be understood that application of the teachings of the present invention to a specific problem or environment will be within the capabilities of one having ordinary skill in the art in light of the teachings contained herein. Examples of the products of the present invention and representative processes for their isolation and manufacture appear above and in the following examples.

EXAMPLES

Example 1

Cloning of a cDNA Complementary to Genomic RNA from HIV-2 Virions

HIV-2 virions were purified from 5 liters of supernatant from a culture of the CEM cell line infected with the ROD isolate and a cDNA first strand using oligo (dT) primer was synthesized in detergent activated endogenous reaction on pelleted virus, as described by M. Alizon et al. in Nature, 312: 757–760 (1984), specifically incorporated herein by reference. RNA-cDNA hybrids were purified by phenol-chloroform extraction and ethanol precipitation. The second-strand cDNA was created by the DNA polymerase I/RNAase H method of Sanger et al. described in Proc. Nat'l. Acad. Sci. USA, 74: 5463–5467 (1977), specifically incorporated herein by reference. The double-stranded cDNA was bluntended with T4 DNA polymerase using a commercial cDNA synthesis kit (obtained from Amersham). After attachment of EcoRI linkers (obtained from Pharmacia), EcoRI digestion, and ligation into EcoRI-digested dephosphorylated M13 tg 130 vector (obtained from Amersham), a cDNA library was obtained by transformation of the E. coli TG1 strain. Recombinant plaques ($10^4$) were screened in situ on replica filters with the 1.5 kb.

HindIII fragment from clone J19, corresponding to the 3' part of the genome of the LAV$_{BRU}$ isolate of HIV-1, $^{32}$p labelled to a specific activity of $10^9$ cpm ug. The filters were prehybridized in 5×SSC, 5× Denhardt solution, 25% formamide, and denatured salmon sperm DNA (100 ug/ml.) at 37° C. for 4 hours and hybridized for 16 hours in the same buffer (Tm −42° C.) plus 4×10$^7$ cpm of the labelled probe (10$^6$ cpm/ml. of hybridization buffer). The washing was done in 5×SSC, 0.1% SDS at 25° C. for 2 hours. 20×SSC is 3M NaCl, 0.3M Na citrate. Positive plaques were purified and single-stranded M13 DNA prepared and end-sequenced according to the method of Sanger et al., supra.

Example 2

Hybridization of DNA from HIV-1 and HIV-2 Infected Cells and RNA from HIV-1 and 2 and SIV Virons with a Probe Derived from an HIV-2 Cloned cDNA DNA was extracted from infected CEM cells continuously producing HIV-1 or 2. The DNA digested with 20 ug of PstI digested with or undigested, was electrophoresed on a 0.8% agarose gel, and Southern-transferred to nylon membrane. Virion dot-blots were prepared in duplicate, as described by F. Clavel et al. in Science 233: 343–346 (1986), specifically incorporated herein by reference, by pelleting volumes of supernatant corresponding to the same amount of reverse transcriptase activity. Prehybridization was done in 50% formamide, 5×SSC, 5× Denhardt solution, and 100 mg./ml. denatured salmon sperm DNA for 4 hours at 42° C. Hybridization was performed in the same buffer plus 10% Dextran sulphate, and 10$^6$ cpm/ml. of the labelled E2 insert (specific activity 10$^9$ cpm/ug.) for 16 hours at 42° C. Washing was in 0.1×SSC, 0.1% SDS for 2×30 mn. After exposition for 16 hours with intensifying screens, the Southern blot was dehybridized in 0.4 N NaOH, neutralized, and rehybridized in the same conditions to the HIV-1 probe labelled to 10$^9$ cpm/ug.

Example 3

Cloning in Lambda Phage of the Complete Provirus DNA of HIV-2

DNA from the HIV-2$_{ROD}$ infected CEM (FIG. 2, lanes a and c) was partially digested with Sau3AI. The 9–15 kb. fraction was selected on a 5–40% sucrose gradient and ligated to BamHI arms of the lambda L47.1 vector. Plaques (2×10$^6$) obtained after in vitro packaging and plating on *E. coli* LA 101 strain were screened in situ with the insert from the E2 cDNA clone. Approximately 10 positive clones were plaque purified and propagated on *E. coli* C600 recBC. The ROD 4, 27, and 35 clones were amplified and their DNA characterized by restriction mapping and Southern blotting with the HIV-2 cDNA clone under stringent conditions, and gag-pol probes from HIV-1 used under non stringent conditions.

Example 4

Sequences of the Coding Regions for the Evelope Protein and GAG Product of the ROD HIV-2 Isolate Additional experimental analysis of the HIV-2 ROD isolate was performed and has yielded the following sequences for the env and gag sequences. Regions coding for amino acid sequences corresponding to known proteins characterized by apparent molecular weights have been identified within the gag sequence: p. 16 (nucleotides 1–405), p. 26 (406–1155) and p. 12 (1156–1566).

Envelope sequence:

MetMetAsnGlnLeuLeuIleAlaIleLeuLeuAlaSerAlaCys
ATGATGAATCAGCTGCTTATTGCCATTTTATTAGCTAGTGCTTGC
 •           •           •           •

LeuValTyrCysThrGlnTyrValThrValPheTyrGlyValPro
TTAGTATATTGCACCCAATATGTAACTGTTTTCTATGGCGTACCC
 •           •           •           •           •

ThrTrpLysAsnAlaThrIleProLeuPheCysAlaThrArgAsn
ACGTGGAAAAATGCAACCATTCCCCTCTTTTGTGCAACCAGAAAT
        100          •           •           •

ArgAspThrTrpGlyThrIleGlnCysLeuProAspAsnAspAsp
AGGGATACTTGGGGAACCATACAGTGCTTGCCTGACAATGATGAT
 •           •           •           •           •           •

TyrGlnGluIleThrLeuAsnValThrGluAlaPheAspAlaTrp
TATCAGCAAATAACTTTGAATGTAACAGAGGCTTTTGATGCATGG
 •                200          •           •           •

AsnAsnThrValThrGluGlnAlaIleGluAspValTrpHisLeu
AATAATACAGTAACAGAACAAGCAATAGAAGATGTCTGGCATCTA
 •           •           •           •           •           •

PheGluThrSerIleLysProCysValLysLeuThrProLeuCys
TTCGAGACATCAATAAAACCATGTGTGAAACTAACACCTTTATGT
 •           •           •          300         •

ValAlaMetLysCysSerSerThrGluSerSerThrGlyAsnAsn
GTAGCAATGAAATGCAGCAGCACAGAGAGCAGCACAGGGAACAAC
 •           •           •           •           •           •

ThrThrSerLysSerThrSerThrThrThrThrThrProThrAsp
ACAACCTCAAAGAGCACAAGCACAACCACAACCACACCCAGAGAG
 •           •           •           •          400

GlnGluGlnGluIleSerGluAspThrProCysAlaArgAlaAsp
CAGGAGCAAGAGATAAGTGAGGATACTCCATGCGCAGCGCGAGAC
 •           •           •           •           •

AsnCysSerGlyLeuGlyGluGluGluThrIleAsnCysGlnPhe
AACTGCTCAGGATTGGGAGAGGAAGAAACGATCAATTGCCAGTTC
 •           •           •           •           •

AsnMetThrGlyLeuGluArgAspLysLysLysGlnTyrAsnGlu
AATATGACAGGATTAGAAAGAGATAAGAAAAAACAGTATAATGAA
       500           •           •           •           •

ThrTrpTyrSerLysAspValValCysGluThrAsnAsnSerThr
ACATGGTACTCAAAAGATGTGGTTTGTGAGACAAATAATAGCACA
 •           •           •           •           •

AsnGlnThrGlnCysTyrMetAsnHisCysAsnThrSerValIle
AATCAGACCCAGTGTTACATGAACCATTGCAACACATCAGTCATC
 •         600           •           •           •

ThrGluSerCysAspLysHisTyrTrpAspAlaIleArgPheArg
ACAGAATCATGTGACAAGCACTATTGGGATGCTATAAGGTTTAGA
 •           •           •           •           •

TyrCysAlaProProGlyTyrAlaLeuLeuArgCysAsnAspThr
TACTGTGCACCACCGGGTTATGCCCTATTAAGATGTAATGATACC
 •           •          700          •           •

AsnTyrSerGlyPheAlaProAsnCyaSerLysValValAlaSer
AATTATTCAGGCTTTGCACCCAACTGTTCTAAAGTAGTAGCTTCT
 •           •           •           •           •

ThrCysThrArgMetMetGluThrGlnThrSerThrTrpPheGly
ACATGCACCAGGATGATGGAAACGCAAACTTCCACATGGTTTGGC
 •           •           •          800          •

PheAsnGlyThrArgAlaGluAsnArgThrTyrIleTyrTrpHis
TTTAATGGCACTAGAGCAGAGAATAGAACATATATCTATTGGCAT

-continued

GlyArgAspAsnArgThrIleIleSerLeuAsnLysTyrTyrAsn
GGCAGAGATAATAGAACTATCATCAGCTTAAACAAATATTATAAT 900

LeuSerLeuHisCysLysArgProGlyAsnLysThrValLysGlu
CTCAGTTTGCATTGTAAGAGGCCAGGGAATAAGACAGTGAAACAA

IleMetLeuMetSerGlyHisValPheHisSerHisTyrGlnPro
ATAATGCTTATGTCAGGACATGTGTTTCACTCCCACTACCAGCCG

IleAsnLysArgProArgGlnAlaTrpCysTrpPheLysGlyLys
ATCAATAAAAGACCCAGACAAGCATGGTGCTGGTTCAAAGGCAAA 1000

TrpLysAspAlaMetGlnGluValLysThrLeuAlaLysHisPro
TGGAAAGACGCCATGCAGGAGGTGAAGACCCTTGCAAAACATCCC

ArgTyrArgGlyThrAsnAspThrArgAsnIleSerPheAlaAla
AGGTATAGAGGAACCAATGACACAAGGAATATTAGCTTTGCAGCG 1100

ProGlyLysGlySerAspProGlyValAlaTyrMetTrpThrAsa
CCAGGAAAAGGCTCAGACCCAGAAGTAGCATACATGTGGACTAAC

CysArgGlyGluPheLeuTyrCysAsnMetThrTrpPheLeuAsn
TGCAGAGGAGAGTTTCTCTACTGCAACATGACTTGGTTCCTCAAT 1200

TrpIleGluAsnLysThrHisArgAsnTyrAlaProCysHisIle
TGGATAGAGAATAAGACACACCGCAATTATGCACCGTGCCATATA

LysGlnIleIleAsnThrTrpHisLysValGlyArgAsnValTyr
AAGCAAATAATTAACACATGGCATAAGGTAGGGAGAAATGTATAT 1300

LeuProProArgGluGlyGluLeuSerCysAsnSerThrValThr
TTGCCTCCCAGGGAAGGGGAGCTGTCCTGCAACTCAACAGTAACC

SerIleIleAlaAsnIleAspTrpGlnAsnAsnAsnGlnThrAsn
AGCATAATTGCTAACATTGACTGGCAAAACAATAATCAGACAAAC

IleThrPheSerAlaGluValAlaGluLeuTyrArgLeuGluLeu
ATTACCTTTAGTGCAGAGGTGGCAGAACTATACAGATTGGAGTTG 1400

GlyAspTyrLysLeuValGluIleThrProIleGlyPheAlaPro
GGAGATTATAAATTGGTAGAAATAACACCAATTGGCTTCGCACCT

ThrLysGluLysArgTyrSerSerAlaHisGlyArgHisThrArg
ACAAAAGAAAAAAGATACTCCTCTGCTCACGGGAGACATACAAGA 1500

GlyValPheValLeuGlyPheLeuGlyPheLeuAlaThrAlaGly
GGTGTGTTCGTGCTAGGGTTCTTGGGTTTTCTCGCAACAGCAGGT

SerAlaMetGlyAlaArgAlaSerLeuThrValSerAlaGluSer
TCTGCAATGGGCGCTCGAGCGTCCCTGACCGTGTCGGCTCAGTGC 1600

ArgThrLeuLeuAlaGlyIleValGlnGlnGlnGlnGlnLeuLeu
CGGACTTTACTGGCCGGGATAGTGCAGCAACAGCAACAGCTGTTG

AspValValLysArgGlnGlnGluLeuLeuArgLeuThrValTrp
GACGTGGTCAAGAGACAACAAGAACTGTTGCGACTGACCGTCTGG 1700

GlyThrLysAsnLeuGlnAlaArgValThrAlaIleGluLysTyr
GGAACGAAAAACCTCCAGGCAAGAGTCACTGCTATAGAGAAGTAG

LeuGlnAspGlnAlaArgLeuAsnSerTrpGlyCysAlaPheArg
CTACAGGACCAGGCGCGGCTAAATTCATGGGGATGTGCGTTTAGA 1800

GlnValCysHisThrThrValProTrpValAsnAspSerLeuAla
CAAGTCTGCCACACTACTGTACCATGGGTTAATGATTCCTTAGCA

ProAspTrpAspAsnMetThrTrpGlnGluTrpGluLysGluVal
CCTGACTGGGACAATATGACGTGGCAGGAATGGGAAAAACAAGTC

ArgTyrLeuGluAlaAsnIleSerLysSerLeuGluGluAlaGln
CGCTACCTGGAGGCAAATATCAGTAAAAGTTTAGAACAGGCACAA 1900

IleGlnGlnGluLysAsnMetTyrGluLeuGlnLysLeuAsnSer
ATTCAGCAAGAGAAAAATATGTATGAACTACAAAAATTAAATAGC

TrpAspIlePheGlyAsnTrpPheAspLeuThrSerTrpValLys
TGGGATATTTTTGGCAATTGGTTTGACTTAACCTCCTGGGTCAAG 2000

TyrIleGlnTyrGlyValLeuIleIleValAlaValIleAlaLeu
TATATTCAATATGGAGTGCTTATAATAGTAGCAGTAATAGCTTTA

ArgIleValIleTyrValValGlnMetLeuSerArgLeuArgLys
AGAATAGTGATATATGTAGTACAAATGTTAAGTAGGCTTAGAAAG 2100

GlyTyrArgProValPheSerSerProProGlyTyrIleGlu***
GGCTATAGGCCTGTTTTCTCTTCCCCCCCCGGTTATATCCAATAG

IleHisIleHisLysAspArgGlyGluProAlaAsnGluGluThr
ATCCATATCCACAAGGACCGGGGACAGCCAGCCAACGAAGAAACA 2200

GluGlnAspGlyGlySerAsnGlyGlyAspArgTyrTrpProTrp
GAAGAAGACGGTGGAAGCAACGGTGGAGACAGATACTGGCCCTGG

ProIleAlaTyrIleHisPheLeuIleArgGlnLeuIleArgLeu
GCGATAGCATATATACATTTCCTGATCCGCCAGCTGATTCGCCTC

LeuThrArgLeuTyrSerIleCysArgAspLeuLeuSerArgSer
TTGACCAGACTATACAGCATCTGCAGGGACTTACTATCCAGGAGC 2300

PheLeuThrLeuGluLeuIleTyrGlnAsnLeuArgAspTrpLeu
TTCCTGACCCTCCAACTCATCTACCAGAATCTCAGAGACTGGCTG

ArgLeuArgThrAlaPheLeuGlnTyrGlyCysGluTrpIleGln
AGACTTAGAACAGCCTTCTTGCAATATGGGTGCGAGTGGATCCAA 2400

GluAlaPheGlnAlaAlaAlaArgAlaThrArgGluThrLeuAla
GAAGCATTCCAGGCCGCCGCGAGGGCTACAAGAGAGACTCTTGCG

GlyAlaCysArgGlyLeuTrpArgValLeuGluArgIleGlyArg
GGCGCGTGCAGGGGCTTGTGGAGGGTATTGGAACGAATCGGGAGG 2500

GlyIleLeuAlaValProArgArgIleArgGlnGlyAlaGlyIle
GGAATACTCGCGGTTCCAAGAAGGATCAGACAGGGAGCAGAAATG

AlaLeuLeu***GlyThrAlaValSerAlaGlyArgLeuTyrGlu
GCCCTCCTGTGAGGGACGGCAGTATCAGCAGGGAGACTTTATGAA 2600

TyrSerMetGluGlyProSerSerArgLysGlyGluLysPheVal
TACTCCATGGAAGGACCCAGCAGCAGAAAGGGAGAAAAATTTGTA

-continued

GlnAlaThrLysTyrGly
GAGGCAACAAAATATGGA

GAG sequence:

MetGlyAlaArgAsnSerValLeuArgGlyLysLysAlaAspGlu
ATGGGCGCGAGAAACTCCGTCTTGAGAGGGAAAAAAGCAGATGAA

LeuGluArgIleArgLeuArgProGlyGlyLysLysLysTyrArg
TTAGAAAGAATCAGGTTACGGCCCGGCGGAAAGAAAAAGTACAGG

LeuLysHisIleValTrpAlaAlaAsnLysLeuAspArgPheGly
CTAAAACATATTGTGTGGGCAGCGAATAAATTGGACAGATTCGGA
100

LeuAlaGluSerLeuLeuGluSerLysGluGlyCysGlnLysIle
TTAGCAGAGAGCCTGTTGGAGTCAAAAGAGGGTTGTCAAAAAATT

LeuThrValLeuAspProMetValProThrGlySerGluAsnLeu
CTTACAGTTTTAGATCCAATGGTACCGACAGGTTCAGAAAATTTA
200

LysSerLeuPheAsnThrValCysValIleTrpCysIleHisAla
AAAAGTCTTTTTAATACTGTCTGCGTCATTTGGTGCATACAGGCA

GluGluLysValLysAspThrGluGlyAlaLysGlnIleValArg
GAAGAGAAAGTGAAAGATACTGAAGGAGCAAAACAAATAGTGCGG
300

ArgHisLeuValAlaGluThrGlyThrAlaGluLysMetProSer
AGACATCTAGTGGCAGAAACAGGAACTGCAGAGAAAATGCCAAGG

ThrSerArgProThrAlaProSerSerGluLysGlyGlyAsnTyr
ACAAGTAGACCAACAGCACCATCTAGCGAGAAGGGAGGAAATTAC
400

ProValGlnHisValGlyGlyAsnTyrThrHisIleProLeuSer
CCAGTGCAACATGTAGGCGGCAACTACACCCATATACCGCTGAGT

ProArgThrLeuAsnAlaTrpValLysLeuValGluGluLysLys
CCCCGAACCCTAAATGCCTGGGTAAAATTAGTAGAGGAAAAAAAG

PheGlyAlaGluValValProGlyPheGluAlaLeuSerGluGly
TTCGGGGCAGAAGTAGTGCCAGGATTTCAGGCACTCTCAGAAGGC
500

CysThrProTyrAspIleAsnGlnMetLeuAsnCysValGlyAsp
TGCACGCCCTATGATATCAACCAAATGCTTAATTGTGTGGGCGAC

HisGlnAlaAlaMetGlnIleIleArgGluIleIleAsnGluGlu
CATCAAGCAGCCATGCAGATAATCAGGGAGATTATCAATGAGGAA
600

AlaAlaGluTrpAspValGlnHisProIleProGlyProLeuPro
GCAGCAGAATGGGATGTGCAACATCCAATACCAGGCCCCTTAGCA

AlaGlyGlnLeuArgGluProArgGlySerAspIleAlaGlyThr
GCGGGGCAGCTTAGAGAGCCAAGGGGATCTGACATAGCAGGGAGA
700

ThrSerThrValGluGluGlnIleGlnTrpMetPheArgProGln
ACAAGCACAGTAGAAGAACAGATCCAGTGGATGTTTAGGCCAGAA

AsnProValProValGlyAsnIleTyrArgArgTrpIleGlnIle
AATCCTGTACCAGTAGGAAACATCTATAGAAGATGGATCCAGATA
800

-continued

GlyLeuGlnLysCysValArgMetTyrAsnProThrAsnIleLeu
GGATTGCAGAAGTGTGTCAGGATGTACAACCCGACCAACATCCTA

AspIleLysGlnGlyProLysGluProPheGlnSerTyrValAsp
GACATAAAACAGGGACCAAAGGAGCCGTTCCAAAGCTATGTAGAT
900

ArgPheTyrLysSerLeuArgAlaGluGlnThrAspProAlaVal
AGATTCTACAAAAGCTTGAGGGCAGAACAAACAGATCCAGCAGTG

LysAsnTrpMetThrGlnThrLeuLeuValGlnAsnAlaAsnPro
AAGAATTGGATGACCCAAACACTGCTAGTACAAAATGCCAACGCA

AspCysLysLeuValLeuLysGlyLeuGlyMetAsnProThrLeu
GACTGTAAATTAGTGCTAAAAGGACTAGGGATGAACCCTACCTTA
1000

GluGluMetLeuThrAlaCysGlnGlyValGlyGlyProGlyGln
GAAGAGATGCTGACCGCCTGTCAGGGCGTAGGTGGGCCAGGCCAG

LysAlaArgLeuMetAlaGluAlaLeuLysGlyValIleGlyPro
AAAGCTAGATTAATGGCAGAGGCCCTGAAAGAGGTCATAGGACCT
1100

AlaProIleProPheAlaAlaAlaGlnGlnArgLysAlaPheLys
GCCCCTATCCCATTCGCAGCAGCCCAGGAGAGAAAGGCATTTAAA

CysTrpAsnCysGlyLysGluGlyHisSerAlaArgGlnCysArg
TGCTGGAACTGTGGAAAGGAAGGGCACTCGGCAAGACAATGCCGA
1200

AlaProArgArgGlnGlyCysTrpLysCysGlyLysProGlyHis
GCACCTAGAAGGCAGGGCTGCTGGAAGTGTGGTAAGCCAGGACAC

IleMetThrAsnCysProAspArgGlnAlaGlyPheLeuGlyLeu
ATCATGACAAACTGCCCAGATAGACAGGCAGGTTTTTTAGGACTG
1300

GlyProTrpGlyLysLysProArgAsnPheProValAlaGlnVal
GGCCCTTGGGGAAAGAAGCCCCGCAACTTCCCCGTGGCCCAAGTT

ProGlnGlyLeuThrProThrAlaProProValAspProAlaVal
CCGCAGGGGCTGACACCAACAGCACCCCCAGTGGATCCAGCAGTG

AspLeuLeuGluLysTyrMetGlnGlnGlyLysArgGlnArgGlu
GATCTACTGGAGAAATATATGCAGCAAGGGAAAAGACAGAGAGAG
1400

GlnArgGluArgProTyrLysGluValThrGluAspLeuLeuHis
CAGAGAGAGAGACCATACAAGGAAGTGACAGAGGACTTACTGCAC

LeuGluGlnGlyGluThrProTyrArgGluProProThrGluAsp
CTCGAGCAGGGGGAGACACCATACAGGGAGCCACCAACAGAGGAG
1500

LeuLeuHisLeuAsnSerLeuPheGlyLysAspGln
TTGCTGCACCTCAATTCTCTCTTTGGAAAAGACCAG

Example 5

Peptide Sequences Encoded by the ENV and GAG Sequences

The following coding regions for antigenic peptides, identified by nucleotide numbers within the gene sequences of Example 4, are of particular interest.

env1 (1735–1809)
```
                             ValThrAlaIleGluLysTyr
                             GTCACTGCTATAGAGAAGTAG
                                •           •

LeuGluAspGlnAlaArgLeuAsnSerTrpGlyCysAlaPheArg
CTACAGGACCAGGCGCGGCTAAATTCATGGGGATGTGCGTTTAGA
    •       •       •       •       •   1004

GlnValCys
CAAGTCTGC
``` env2 (1912–1983)
```
                       SerLysSerLeuGluGlnAlaGln
                       AGTAAAAGTTTAGAACAGGCACAA
                              •           •

IleGlnGlnGluLysAsnMetTyrGluLeuGlnLysLeuAsnSer
ATTCAGCAAGAGAAAAATATGTATGAACTACAAAAATTAAATAGC
  1940     •       •       •       •

Trp
TGG
``` env3 (1482–1530)
```
ProThrLysGluLysArgTyrSerSerAlaHisGlyArgHisThrArg
CCTACAAAAGAAAAAAGATACTCCTCTGCTCACGGGAGACATACAAGA
    •        1500     •        •        •
``` env4 (55–129)
```
         CysThrGlnTyrValThrValPheTyrGlyValPro
         TGCACCCAATATGTAACTGTTTTCTATGGCGTACCC
             •       •       •       •

ThrTrpLysAsnAlaThrIleProLeuPheCysAlaThr
ACGTGGAAAAATGCAACCATTCCCCTCTTTTGTGCAACC
        100     •       •
``` env5 (175–231)
```
                                    AspAsp
                                    GATGAT
                                       •

TyrGluGluIleThrLeuAsnValThrGluAlaPheAspAlaTrp
TATCAGGAAATAACTTTGAATGTAACAGAGGCTTTTGATGCATGG
           •       200     •       •

AsnAsn
AATAAT
``` env6 (274–330)
```
     GluThrSerIleLysProCysValLysLeuThrProLeuCys
     GAGACATCAATAAAACCATGTGTGAAACTAACACCTTTATGT
         •       •        300     •

ValAlaMetLysCys
GTAGCAATGAAATGC
     •       •
``` env7 (607–660)
```
                        AsnHisCysAsnThrSerValIle
                        AACCATTGCAACACATCAGTCATC
                          610     •       •

ThrGluSerCysAspLysHisTyrTrpAsp
ACAGAATCATGTGACAAGCACTATTGGGAT
     •       •       •
``` env8 (661–720)
```
                            AlaIleArgPheArg
                            GCTATAAGGTTTAGA
                                  •

TyrCysAlaProProGlyTyrAlaLeuLeuArgCysAsnAspThr
TACTGTGCACCACCGGGTTATGCCCTATTAAGATGTAATGATACC
    •       •       700     •       •
``` env9 (997–1044)
```
      LysArgProArgGlnAlaTrpCysTrpPheLysGlyLys
      AAAAGACCCAGACAAGCATGGTGCTGGTTCAAAGGCAAA
                  1000     •       •       •
TrpLysAsp
TGGAAAGAC
``` env10 (1132–1215)
```
      LysGlySerAspProGluValAlaTyrMetTrpThrAsn
      AAAGGCTCAGACCCAGAAGTAGCATACATGTGGACTAAC
         •        •       •       •        •

CysArgGlyGluPheLeuTyrCysAsnMetThrTrpPheLeuAsn
TGCAGAGGAGAGTTTCTCTACTGCAACATGACTTGGTTCCTCAAT
    •       •       1200     •       •
``` env11 (1237–1305)
```
                          ArgAsnTyrAlaProCysHisIle
                          CGCAATTATGCACCGTGCCATATA
                             •       •       •

LysGlnIleIleAsnThrTrpHisLysValGlyArgAsnValTyr
AAGCAAATAATTAACACATGGCATAAGGTAGGGAGAAATGTATAT
    •       •       •        1300
``` gag1 (991–1053)
```
AspCysLysLeuValLeuLysGlyLeuGlyMetAsnProThrLeu
GACTGTAAATTAGTGCTAAAAGGACTAGGGATGAACCCTACCTTA
    •        1000      •       •       •

GluGluMetLeuThrAla
GAAGAGATGCTGACCGCC
     •       •
```

Of the foregoing peptides, env1, env2, env3 and gag1 are particularly contemplated for diagnostic purposes, and env4, env5, env6, env7, env8, env9, env10 and env11 are particularly contemplated as protecting agents. The foregoing peptides can be synthesized by conventional protein synthesis techniques, such as that of Merrified.

It will be apparent to those skilled in the art that various modifications and variations can be made in the processes and products of the present invention. Thus, it is intended that the present application cover the modifications and variations of this invention provided they come within the scope of the appended claims and their equivalents.

What is claimed is:

1. A recombinant or synthetic peptide consisting of the following amino acid sequence:

Ser Lys Ser Leu Glu Gln Ala Gln Ile Gln Gln Glu Lys Asn Met Tyr Glu Leu Gln Lys Leu Asn Ser Trp, wherein said peptide constitutes an env2 peptide of HIV-2.

2. A recombinant or synthetic peptide consisting of the following amino aced sequence:

(a) Ser Lys Ser Leu Glu Gln Ala Gln Ile Gln Gln Glu Lys Asn Met Tyr Glu Leu Gln Lys Leu Asn Ser Trp, or (b) corresponding peptides of an env2 peptide of an HIV-2 virus chosen from HIV-2 viruses deposited at the COLLECTION NATIONALE DES CULTURES DE MICRO-ORGANISMES (CNCM) under No. I-502, No. I-642, and No. I-643, wherein said corresponding peptide is 24 amino acids in length, and is encoded by nucleotides 1912–1983 of the env gene, wherein said numbering scheme is based upon the prototypical HIV-2 isolate ROD.

3. A recombinant or synthetic peptide comprising the following amino acid sequence:

(a) Ser Lys Ser Leu Glu Gln Ala Gln Ile Gln Gln Glu Lys Asn Met Tyr Glu Leu Gln Lys Leu Asn Ser Trp, wherein said peptide constitutes a env2 peptide of HIV-2.

4. A recombinant or synthetic peptide comprising a peptide consisting of the following amino acid sequence:
   (a) Ser Lys Ser Leu Glu Gln Ala Gln Ile Gln Gln Glu Lys Asn Met Tyr Glu Leu Gln Lys Leu Asn Ser Trp or
   (b) corresponding peptides of an env2 peptide of an HIV-2 virus selected from the group of HIV-2 viruses deposited at the COLLECTION NATIONALE DES CULTURES DE MICRO-ORGANISMES (CNCM) under No. I-502, No. I-532, No. I-642, and No. I-643, wherein said corresponding peptide is 24 amino acids in length, and is encoded by nucleotides 1912–1983 of the env gene, wherein said numbering scheme is based upon the prototypical HIV-2 isolate ROD.

5. A method of assaying for the presence of anti-HIV-2 antibodies in a body fluid sample comprising the following steps:

(a) admixing a body fluid sample with an antigen, wherein the antigen is a peptide of any one of claims 1–4;

(b) allowing the antigen and the anti-HIV-2 antibodies present in the body fluid sample to form an antigen-antibody immune complex;

(c) detecting the presence of anti-HIV-2 antibodies in said antigen-antibody immune complex; and (d) comparing the antigen-antibody immune complex results with at least one HIV-2 negative or positive sample as a control.

6. The method according to claim 5, further comprising detecting the antigen-antibody immune complex with a labeled antibody that binds to the anti-HIV-2 antibodies present in the antigen-antibody immune complex.

7. A diagnostic kit for detecting the presence or absence of anti-HIV-2 antibodies, comprising:

a) at least one peptide of HIV-2 selected from the peptides of any one of claims 1–4, wherein the peptide is present in an amount sufficient to perform said detection;

b) at least one reagent for detecting the formation of an immune complex between at least one peptide and anti-HIV-2 antibodies; and c) at least one vial or container for use in a diagnostic kit.

8. The diagnostic kit according to claim 7, further comprising a labeled reagent for the detection of an antigen-antibody immune complex.

9. The method according to claim 6, wherein at least one assay chosen from immunofluorescence assays, radioimmunoassays, and Western Blot tests is used to detect the presence of anti-HIV-2 antibodies in said antigen-antibody immune complex.

* * * * *

UNITED STATES PATENT AND TRADEMARK OFFICE
CERTIFICATE OF CORRECTION

PATENT NO. : 6,979,535 B2 Page 1 of 1
DATED : December 27, 2005
INVENTOR(S) : Marc Alizon et al.

It is certified that error appears in the above-identified patent and that said Letters Patent is hereby corrected as shown below:

Title page,
Item [75], Inventors, "Pierre Sonigo, Gutenberg (FR);" should read -- Pierre Sonigo, Paris (FR); --; and "Mireille Guyader, Laugier (FR)" should read -- Mireille Guyader, Paris (FR) --.

Signed and Sealed this

Seventh Day of March, 2006

JON W. DUDAS
*Director of the United States Patent and Trademark Office*